United States Patent
O'Donnell

(10) Patent No.: US 7,449,025 B1
(45) Date of Patent: Nov. 11, 2008

(54) SURGICAL INSTRUMENT TO SECURE BODY TISSUES

(76) Inventor: Pat D. O'Donnell, 1427 E. 35th St., Tulsa, OK (US) 74105

( * ) Notice: Subject to any disclaimer, the term of this patent is extended or adjusted under 35 U.S.C. 154(b) by 1104 days.

(21) Appl. No.: 10/321,814

(22) Filed: Dec. 17, 2002

(51) Int. Cl.
*A61B 17/04* (2006.01)
(52) U.S. Cl. .................................................. 606/232
(58) Field of Classification Search ............... 606/232, 606/73, 72, 75, 95; 623/13.14
See application file for complete search history.

(56) References Cited

U.S. PATENT DOCUMENTS

| | | | | |
|---|---|---|---|---|
| 5,059,206 A | * | 10/1991 | Winters | 606/213 |
| 5,486,197 A | | 1/1996 | Le et al. | 606/232 |
| 5,720,753 A | | 2/1998 | Sander et al. | 606/104 |
| 5,720,766 A | | 2/1998 | Zang et al. | 606/232 |
| 5,725,541 A | | 3/1998 | Anspach, III et al. | 606/151 |
| 5,895,396 A | | 4/1999 | Day et al. | 606/151 |
| 5,968,045 A | * | 10/1999 | Frazier | 606/73 |
| 5,968,078 A | | 10/1999 | Grotz | 606/232 |
| 5,993,477 A | * | 11/1999 | Vaitekunas et al. | 606/232 |
| 6,096,060 A | | 8/2000 | Fitts et al. | 606/232 |
| 6,200,330 B1 | | 3/2001 | Benderev et al. | 606/232 |
| 6,290,702 B1 | * | 9/2001 | Fucci et al. | 606/72 |
| 6,319,270 B1 | | 11/2001 | Grafton et al. | 606/232 |
| 6,355,066 B1 | * | 3/2002 | Kim | 623/13.14 |
| 6,387,041 B1 | | 5/2002 | Harari et al. | 606/30 |
| 6,692,499 B2 | * | 2/2004 | Tormala et al. | 606/72 |
| 6,743,232 B2 | * | 6/2004 | Overaker et al. | 606/72 |
| 2002/0019649 A1 | | 2/2002 | Sikora et al. | 606/232 |
| 2002/0072806 A1 | | 6/2002 | Buskirk et al. | 623/23.51 |

* cited by examiner

*Primary Examiner*—Todd E. Manahan
*Assistant Examiner*—Tuan V Nguyen
(74) *Attorney, Agent, or Firm*—Winstead, P.C.

(57) ABSTRACT

In a first embodiment, a surgical instrument for securing body tissue comprising an anchoring member formed from organic or inorganic biocompatible material having head, shaft and tip portions, the shaft portion comprising at least two generally opposed outwardly flaring fins with each of the fins having angularly displaced distal and proximal ends for piercing body tissue. In a second embodiment, the instant invention comprises a surgical instrument for securing body tissue comprising an anchoring member formed from organic or inorganic biocompatible material having head, shaft and tip portions, the shaft portion comprising at least two generally opposed outwardly flaring fins with each of the fins having angularly displaced distal and proximal ends for piercing body tissue and a central bore portion positioned within the interior portion of the shaft portion instrument extending from the head portion through the tip portion.

3 Claims, 7 Drawing Sheets

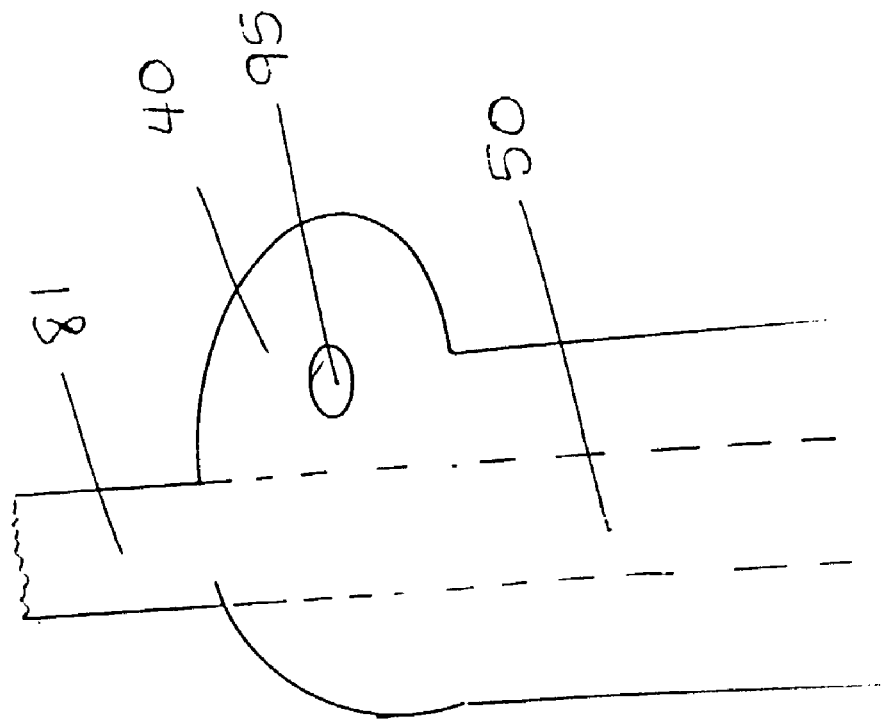
Figure 4.1
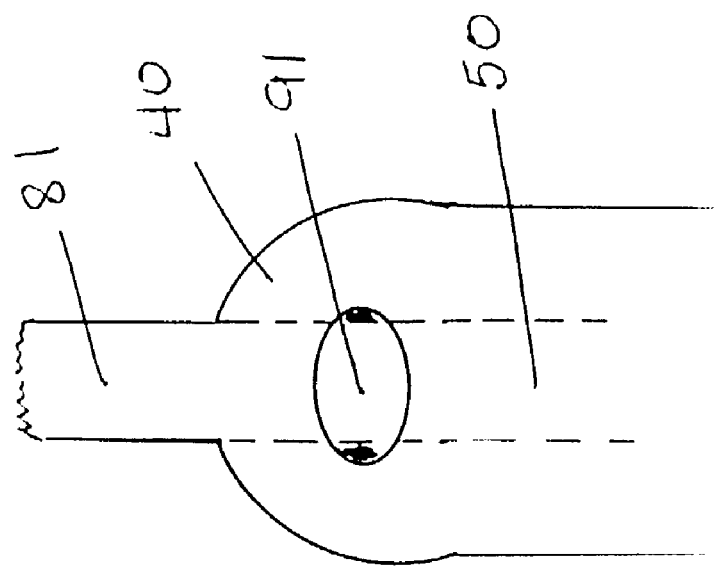
Figure 4

SURGICAL INSTRUMENT TO SECURE BODY TISSUES

REFERENCE TO PENDING APPLICATIONS

This application is not related to any pending applications.

REFERENCE TO MICROFICHE APPENDIX

This application is not referenced in any microfiche appendix.

TECHNICAL FIELD OF THE INVENTION

The present invention relates generally to surgical affixation devices and more particularly to a surgical instrument that is secured and positioned within tissues by a plurality of outwardly flaring fins located along a shaft of the instrument which affixes or otherwise connects synthetic material or human tissues including epithelium, connective muscle and nerve tissues.

BACKGROUND OF THE INVENTION

There are four basic tissues of the body; epithelium, connective (bone, cartilage, fascia and fat), muscle, and nerve tissue. Surgical procedures that restore or maintain anatomical support of body tissues usually involve re-attachment of connective tissues. The most common clinical application of re-attachment of connective tissues is closure of a surgical wound using standard surgical suturing. For surgical procedures involving bone tissue, metal screws and metal pins are often used because of the density of bone tissue. When tissues of different types are attached together such as ligaments to bone, a combination of bone screws and ligament sutures are usually used. Accurate intra operative position of tissue attachment is often compromised by the technical difficulty in placement of the tissue approximating device such as a bone screw with a pre-loaded suture.

Intra operative use of metal bone screws in clinical applications that have a potential for infection has resulted in wound infections requiring surgical removal of the bone screws and other non-absorbable products that can represent a foreign body nidus for continued infection. When feasible, biodegradable products are being used in intra operative clinical applications to avoid problems related to non-absorbable products.

A tissue anchor that can be accurately positioned and placed easily is needed for approximating tissues intra operatively. A need addressed and exceeded according to the teachings of the instant invention.

BRIEF SUMMARY OF THE INVENTION

The present invention specifically addresses and alleviates the afore-noted deficiencies in the art. In this regard, the present invention is directed to novel devices for the attachment of sutures, grafts and other types of tissues and materials to bone, ligaments, fascia and soft tissue as may be warranted in a given surgical procedure.

A tissue anchor is disclosed that has circumferential rows of anchoring fins along the shaft of the anchor. The shaft can be solid or open containing an introducer. The length and diameter of the shaft of the anchor can be appropriately dimensioned for varying clinical applications. The number of rows of fins, the length of the fins, shape of the fins and the height of the fins can also vary according to clinical application. The fins are placed on the shaft at a preferred angle between distal and proximal ends of approximately 10 degrees. The angle of the fins allows the tip of the fins to be slightly offset from the entrance tract. In some clinical applications, the angle of the fins on the shaft can be greater or less. The composition of the anchors can be any biocompatible organic (carbon containing molecule) material or any biocompatible inorganic material (non-carbon containing molecule) which include biodegradable and non-biodegradable polymers as well as metal including steel and titanium.

The head of the solid shaft tissue anchor is shaped to fit an introducer of the same shape allowing for pre-loaded sutures to be placed with the anchor. A central channel through the head and upper segment is an embodiment of the solid shaft tissue anchor to provide stabilization of the anchor during intra operative positioning.

The head of the open shaft anchor has a channel for the introducer which also fits the shape of the head allowing the pre-loaded sutures to be placed with the anchor. The introducer can have different handle shapes according to the clinical application.

The tissue anchor head may have many shapes for different clinical applications. A central eyelet or offset eyelet is the preferred for suture placement. A hook head can be used for suture placement after the tissue anchor has been positioned. A cartwheel head or nail head can be used for attaching tissues without sutures. These may be used for attaching biocompatible materials to tissues. A hemi-cartwheel head and hemi-nail head can be used in selected clinical applications.

The tissue fin anchors can be used intra operatively in a wide range of surgical requirements because of the many different tissues that can be approximated using the fin anchors. The tissue fin anchors can be constructed to attach any connective tissue to any other type of connective tissue. Tissue fin anchors can be constructed for use in fatty tissue as well as fascia and bone. For soft tissue applications, the fin anchors can be placed quickly and accurately. The length of the anchors, the fin number and size allows the tissue fin anchor to be structured for attaching tissues intra operatively that have previously required conventional hand suturing. For clinical applications in bone requiring drilling a hole, the tissue fin anchor can be pressed into position without requiring a bone screwing device. For intra operative attachment of ligaments to bone, fascia to bone, or biocompatible synthetic materials to any other tissues, the tissue fin anchor is constructed specifically for the application and can be placed quickly and accurately to provide efficient and precise intra operative positioning of the anchor.

An object of the present invention is to provide surgical implantation devices for the attachment of sutures, grafts, tissues and the like to bone, connective tissue and soft tissue that can be utilized in a wide variety of surgical procedures.

Another object of the present invention is to provide devices for the affixation of sutures, grafts, tissues and the like to bone, connective tissue and soft tissue at a specific site or location.

Another object of the present invention is to provide devices for the attachment of sutures, grafts, tissues and the like to bone, connective tissue and soft tissue at a specific location that are less traumatic than other prior art affixation devices.

A further object of the present invention is to provide devices for the attachment of sutures, grafts, tissues and the like to bone, connective tissue and soft tissue at a specific location that are easily attachable to and detachable from a point of fixation than prior art devices and re-attachable as may be necessary for a given procedure or future procedures.

It is yet another object of the instant invention to disclose a tissue anchor that has circumferential rows of anchoring fins along a solid shaft of the anchor.

An additional object of the instant invention is to disclose a tissue anchor that has circumferential rows of anchoring fins along an open shaft anchor dimensioned to contain an introducer.

A further object of the instant invention is to have circumferential rows of anchoring fins which are placed on the shaft at a preferred angle between distal and proximal ends of approximately 10° which allows the tip of the fins to be slightly offset from the entrance track.

Another object of the instant invention is to disclose an anchor with fins extending from a shaft which is comprised of any biocompatible organic material or any biocompatible inorganic material.

Still another object of the instant invention is to disclose a tissue anchor which has a central bore through the head and upper segment of a solid shaft to provide stabilization of the anchor during intra operative positioning.

A yet further object of the instant invention is to disclose a tissue anchor with a head portion which may comprise a central eyelet or offset eyelet.

A further object of the instant invention is to disclose a tissue anchor wherein a hook head can be used for suture placement after the tissue anchor has been positioned.

Yet another object of the instant invention is to disclose a cartwheel head or nail head that can be used for attaching tissues without sutures.

Another object of the instant invention is to disclose a tissue anchor wherein the tissue fin anchors can be constructed to attach any connective tissue to any other type of connective tissue.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

In this respect, before explaining at least one embodiment of the invention in detail, it is to be understood that the invention is not limited in this application to the details of construction and to the arrangement so the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Further, the purpose of the foregoing abstract is to enable the U.S. Patent and Trademark Office and the public generally, and especially the design engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Additional objects and advantages of the invention are set forth, in part, in the description which follows and, in part, will be apparent to one of ordinary skill in the art from the description and/or from the practice of the invention.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings, depictions and descriptive matter in which there is illustrated preferred embodiments and results of the invention.

BRIEF DESCRIPTION OF THE DRAWINGS

FIGS. 4 through 6 illustrate various anchor head and suturing groove combinations adaptively used in association with the anchors illustrated in FIGS. 1 and 2.

DETAILED DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is clear that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

Figure 1:
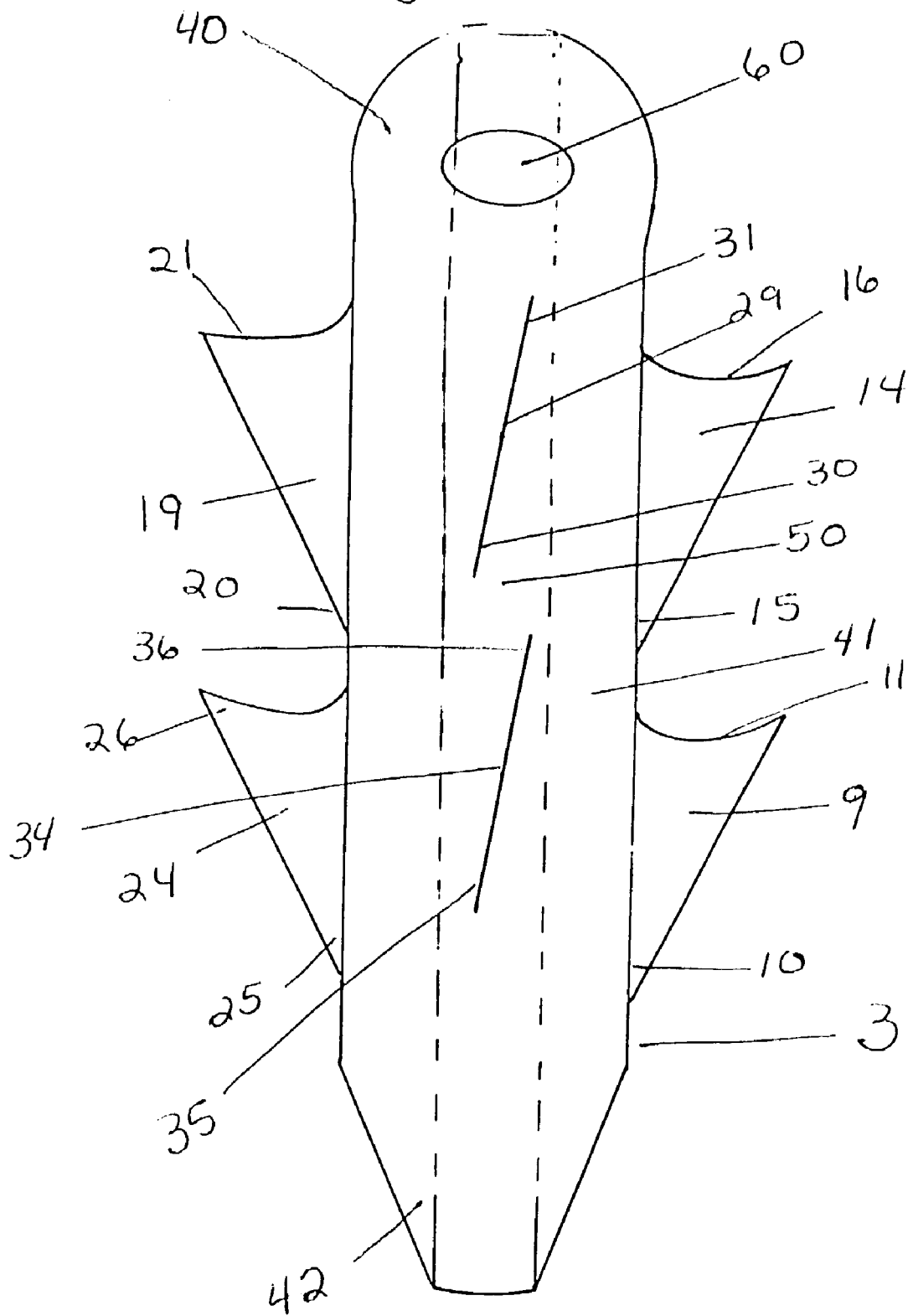
FIG. 1 is a perspective view of the open shaft anchor embodiment of the instant invention.

FIG. 1 is a perspective view of an open shaft anchor embodiment of the instant invention. Turning now to FIG. 1.

In FIG. 1 the tissue fin anchor is generally referred to as element 3 and is comprised of a head portion 40, shaft portion 41 and tip portion 42. The shaft portion 41 is further comprised of a plurality generally opposed outward flaring fins (9, 14, 19, 24, 29, 34) with each of said fins having angularly displaced distal and proximal ends (10, 11, 15, 16, 20, 21, 25, 26, 35, 36, 30 and 31 respectively). As can be seen in FIG. 1, the angularly displaced fins are shown positioned on said shaft 41 at an angle of approximately 10° (best observed fin 34, distal end 35 versus proximal end 36 and fin 29 and distal end 30, proximal end 31). It will be appreciated by those skilled in the art that the tissue anchor length, anchor diameter, number of rows of fins, length of fins, curvature of distal end surface, height of fins, angle of fins, number of fins in each row and arrangement of fins on the shaft can and should vary according to clinical application. As an illustrative but non-limiting application example, bone is a very dense tissue would require a small anchor with small fins while fat is a very soft tissue and requires a longer anchor with large fins and additional rows of fins. The head portion 40 further comprises an eyelet accommodation 60 through which a suture may be inserted. In an alternative embodiment, a hook or other similarly intended attachment means may be provided for a suture and will be discussed further in association with FIGS. 4 through 8. Returning to FIG. 1 there is also disclosed central bore portion 50 positioned within the interior portion of shaft 41 and extends from the anchors head portion 40 through its tip portion 42.

Figure 2:
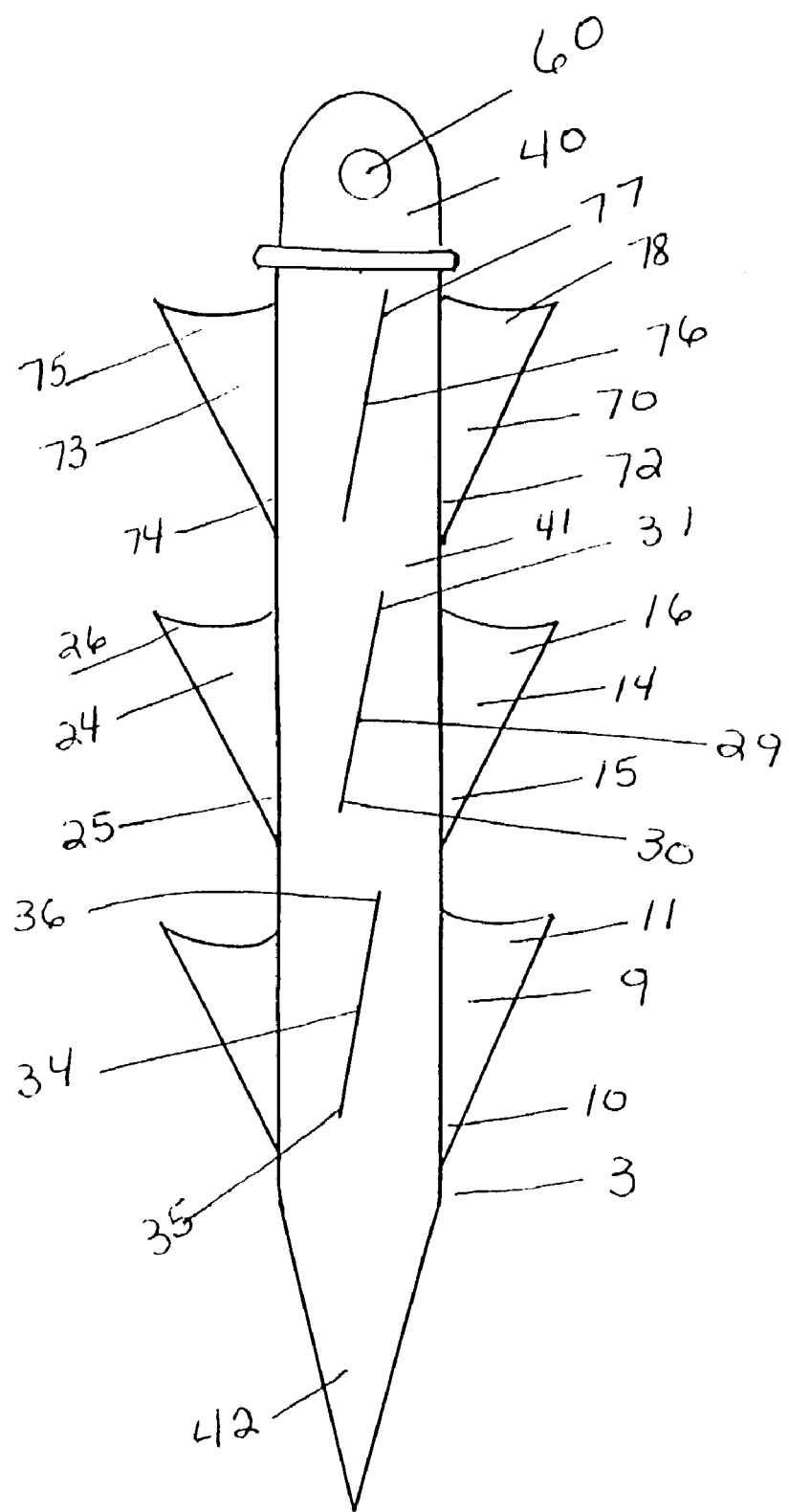
FIG. 2 is a perspective view of the solid shaft tissue anchor of the instant invention.

FIG. 2 is a perspective view of the solid shaft tissue anchor embodiment of the instant invention. Turning now to FIG. 2.

In FIG. 2 the tissue fin anchor is generally referred to as element 3 and is comprised of head portion 40, shaft portion 41 and tip portion 42. The shaft portion 41 is further comprised of a plurality generally opposed outward flaring fins (9, 14, 24, 34, 70, 73) with each of said fins having angularly displaced distal and proximal ends (25, 26, 35, 36, 74, 75, 72, 78, 15, 16, 10 and 11 respectively). As can be seen in FIG. 2, the angularly displaced fins are shown positioned on said shaft 41 at an angle of approximately 10° (best observed fin 34, distal end 35 versus proximal end 36 and fin 29, distal end 30, proximal end 31). It will be appreciated by those skilled in the art that the tissue anchor length, anchor diameter, number of rows of fins, length of fins, height of fins, angle of fins, number of fins in each row and arrangement of fins on the shaft can and should vary according to clinical application. The head portion 40 further comprises an eyelet accommodation 60 through which a suture may be inserted. In an alternative embodiment, a hook or other similarly intended attachment means may be provided for a suture and will be discussed further in association with FIGS. 4 through 8. In a readily envisioned alternative embodiment of the instant invention as disclosed in FIG. 2, a central bore may be positioned within the upper interior portion of said shaft portion and extending generally from said upper interior portion through the upper head portion. Also disclosed in FIG. 2 is an embodiment of the instant invention where additional rows of fins have been provided to allow the anchor as illustrated in FIG. 2 to be used in association with very soft tissue, such as fat.

Figure 3:
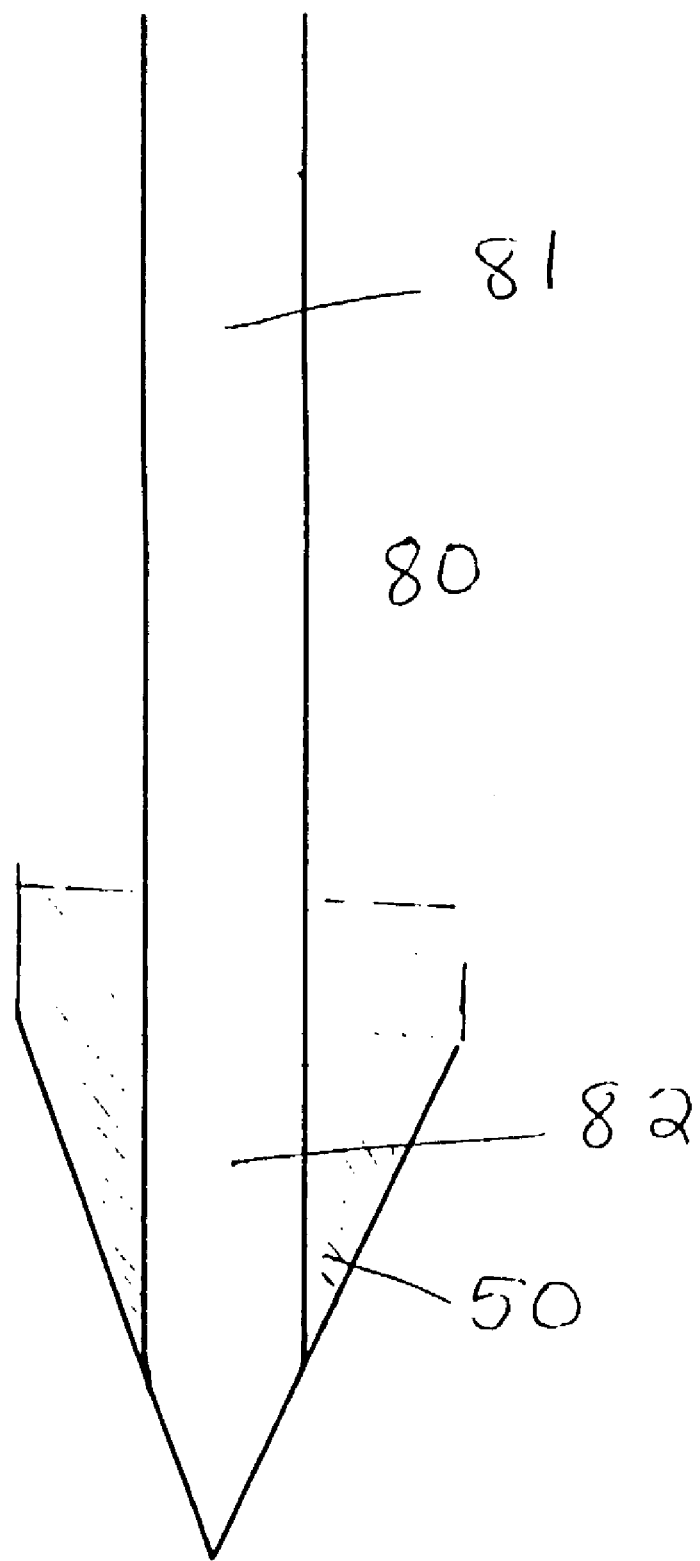
FIG. 3 is the insertion device used in association with the anchor of FIG. 1.

FIG. 3 is the insertion device used in association with the open shaft anchor embodiment discussed and disclosed in association with FIG. 1. Turning now to FIG. 3. In FIG. 3 the insertion member 80 is shown and is comprised of an insertion member shaft 81 and tip portion 82 wherein said tip portion 82 is appropriately dimensioned to allow its insertable accommodation within the central bore portion 50 of anchor 3.

Figure 5A:
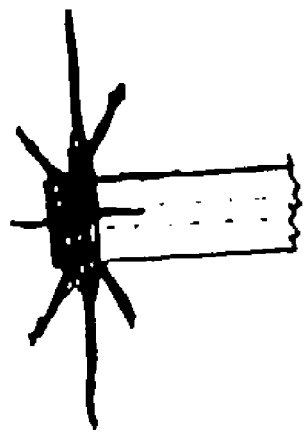
Figure 5:
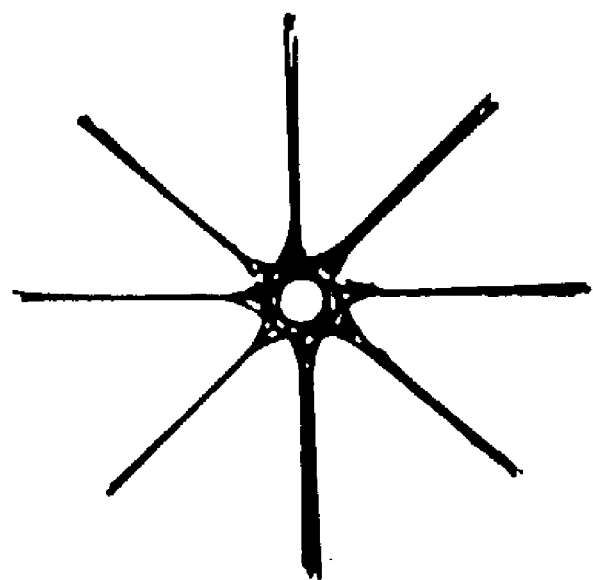
Figure 6:

FIGS. 4 through 6 illustrate various anchor head and suturing groove combinations adaptively used in association with the anchors illustrated in FIGS. 1 and 2. Turning now to FIGS. 4 and 4A.

As seen in FIGS. 4 and 4A, head of anchor 3 can have a centrally positioned eyelet 91 or offset positioned eyelet 95. Said head portion 40 adaptable to possess or not possess an attached pre-loaded suture. Also shown in association with FIGS. 4 and 4A for purposes of full and enabling disclosure is the central bore 50 of the embodiment of the invention illustrated and discussed in association with FIG. 1 and the introducer shaft 81 discussed and disclosed in association with FIG. 3.

Figure 6A:

FIGS. 5 through 6A illustrate alternative anchor heads which can be used in association with the anchor of embodiments disclosed in FIGS. 1 and 2 to utilize said anchors as a tissue tack wherein FIGS. 5 and 5A illustrates cartwheel head used in association with the anchors of FIGS. 1 and 2 to use as a tack and FIGS. 6 and 6A illustrate a nail or hemi-nail head configuration respectively.

Figure 7:
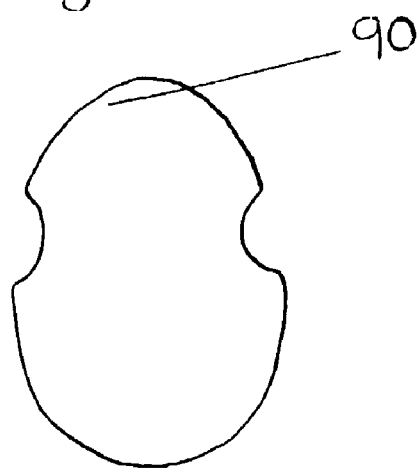
FIGS. 7 and 7A illustrate alternative anchor head configurations when utilizing an anchor of the instant invention as a tissue tack.
Figure 7A:
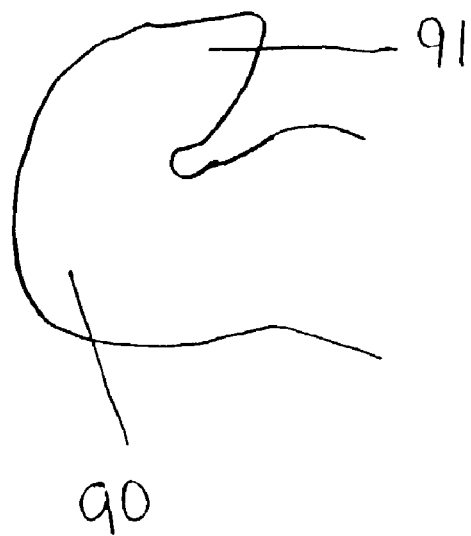

FIGS. 7 and 7A illustrates a hook-like head anchor of the instant invention as discussed and disclosed in association with FIGS. 1 and 2 wherein said hook-like structure 91 may be used for the positioning in association therewith of a suture.

Figure 8:
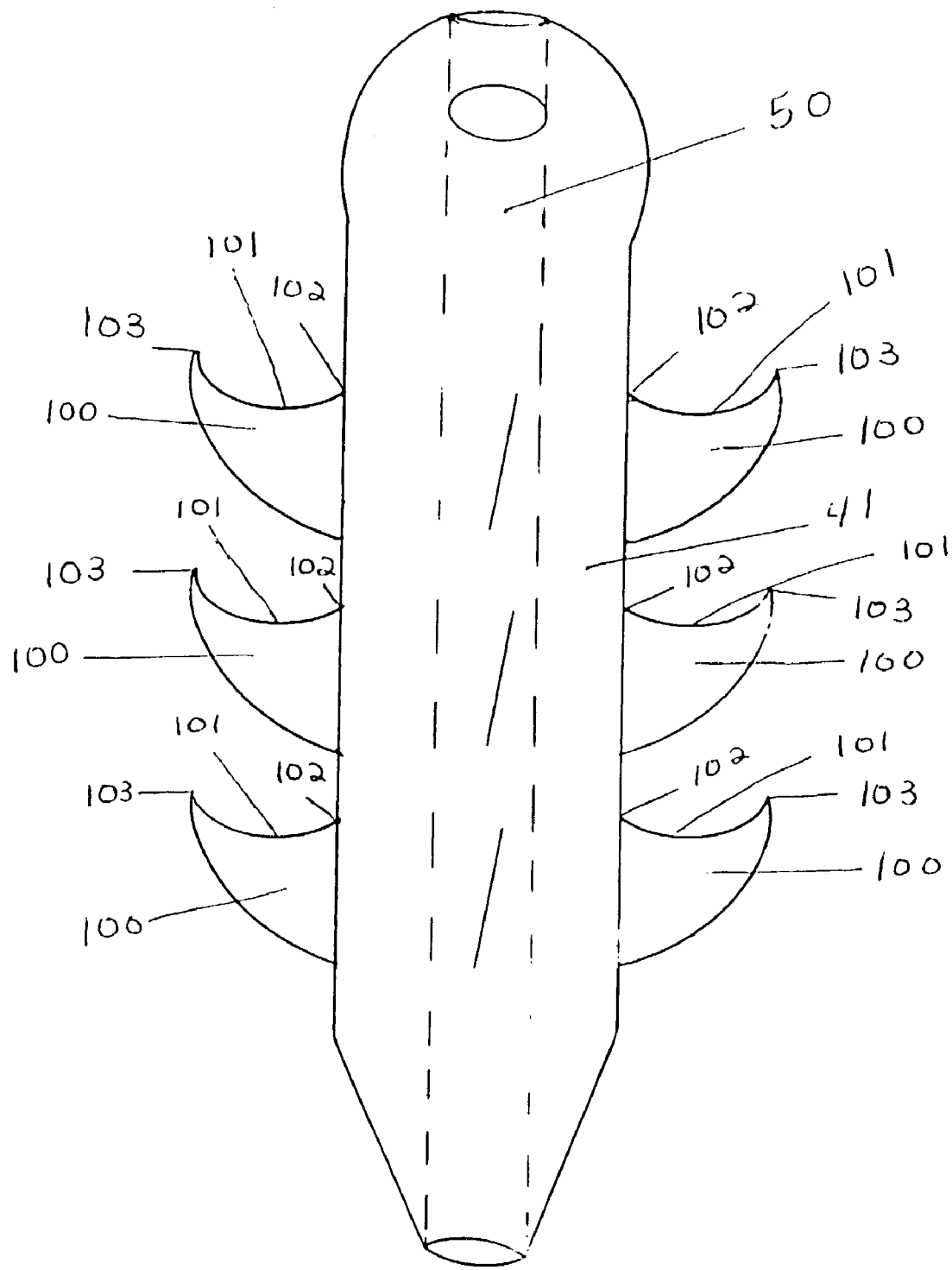
FIG. 8 illustrates an alternative embodiment of the open shaft anchor of FIG. 1 wherein the anchor of the instant invention comprises fins which embody an exaggerated curvature along each of said fins most proximal surface.

FIG. 8 illustrates an alternative embodiment of the open shaft anchor of FIG. 1 wherein the anchor of the instant invention comprises an exaggerated curvature on the most proximal edge of each of said fins. Turning now to FIG. 8. In FIG. 8 is disclosed the embodiment illustrated in association with FIG. 1 further comprising fin-like structures 100 with an exaggerated curvature extending along each of anchor's fins most proximal surface 101 and extending from the point 102 where each of said fins is joined to shaft 41 and extending outwardly along each of said fins most proximal surface to the end of each of said fins outward most tip 103.

It will be apparent to those skilled in the art that various modifications and variations can be made in the construction, configuration, and/or operation of the present invention without departing from the scope or spirit of the invention. For example, in the embodiments mentioned above, variations in the materials used to make each element of the invention may vary without departing from the scope of the invention. Thus, it is intended that the present invention cover the modifications and variations of the invention provided they come within the scope of the appended claims and their equivalents.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

What is claimed is:

1. A surgical instrument for securing body tissue comprising:
   an anchoring member formed from organic or inorganic biocompatible material having head, shaft and tip portions,
   said anchoring member having a substantially central longitudinal axis extending substantially between said head portion and said tip portion of said anchoring member;
   said shaft portion comprising at least two generally outwardly flaring fins with each of said fins having a proximal portion, a distal portion and a side that, in its entirety, is directly coupled to said shaft, said side having a substantially central longitudinal axis extending substantially between said proximal portion and said distal portion; and said longitudinal axis of each fin configured in non-parallel orientation to said longitudinal axis of said anchoring member;

wherein said head portion further comprises a centrally positioned eyelet accommodation through which a suture may be inserted.

2. A surgical instrument for securing body tissue comprising:

an anchoring member formed from organic or inorganic biocompatible material having head, shaft and tip portions, said anchoring member having a substantially central longitudinal axis extending substantially between said head portion and said tip portion of said anchoring member;

said shaft portion comprising:

at least two generally outwardly flaring fins with each of said fins having a proximal portion, a distal portion and a side that, in its entirety, is directly coupled to said shaft, said side having a substantially central longitudinal axis extending substantially between said proximal portion and said distal portion; and a central bore portion positioned within the interior portion of said shaft portion instrument extending from said head portion through said tip portion; and said longitudinal axis of each fin configured in non-parallel orientation to said longitudinal axis of said anchoring member;

wherein said head portion further comprises a centrally positioned eyelet accommodation through which a suture may be inserted.

3. The surgical instrument of claim 2 further comprising an insertion member, said insertion member dimensioned to allow its insertable accommodation within said central bore portion.

* * * * *